(12) United States Patent
David et al.

(10) Patent No.: US 6,450,167 B1
(45) Date of Patent: Sep. 17, 2002

(54) INTRAORAL DEVICE

(76) Inventors: Michel David, 23 rue Bony, Lyon (FR), 69004; Dominique Robert, 11 impasse de l'Ecluse, Caluire (FR), 69300; Thierry Petitjean, 12 avenue de Limburg, Sainte-Foy-les-Lyon (FR), 69110

( * ) Notice: Subject to any disclaimer, the term of this patent is extended or adjusted under 35 U.S.C. 154(b) by 0 days.

(21) Appl. No.: 09/011,240
(22) PCT Filed: Jul. 25, 1996
(86) PCT No.: PCT/FR96/01175
§ 371 (c)(1),
(2), (4) Date: Jun. 11, 1998
(87) PCT Pub. No.: WO97/04716
PCT Pub. Date: Feb. 13, 1997

(30) Foreign Application Priority Data

Jul. 31, 1995 (FR) .............................. 95/09490

(51) Int. Cl.$^7$ .................................................. A61F 5/56
(52) U.S. Cl. ........................ 128/848; 128/859; 602/902
(58) Field of Search .................... 128/846, 848, 128/859–862; 433/6, 69; 602/902

(56) References Cited

U.S. PATENT DOCUMENTS

| 4,505,672 A | * | 3/1985 | Kurz ............................ 433/6 |
| RE33,442 E | * | 11/1990 | George ...................... 128/860 |
| 5,409,017 A | * | 4/1995 | Lowe ......................... 128/848 |
| 5,427,117 A | * | 6/1995 | Thornton .................... 128/848 |
| 5,755,219 A | * | 5/1998 | Thornton .................... 128/848 |
| 6,109,265 A | * | 8/2000 | Frantz ........................ 128/848 |

* cited by examiner

*Primary Examiner*—Michael A. Brown
(74) *Attorney, Agent, or Firm*—Millen, White, Zelano & Branigan, P.C.

(57) ABSTRACT

Intrabuccal device includes two shells (2, 3) made of thermoformed plastic material, the first of which respectively covers the superior arch, and the second of which covers the inferior arch of the oral cavity. This device is provided with (rings and arms) (4a, 4b, 13a, 13b) that act on the said shells (2, 3) and can generate a mandibular propulsion force oriented in the direction of the mandibular propulsion and in the posteroanterior sense, so as to keep a shift of the mandible to the front of the maxilla, while allowing lateral movements.

16 Claims, 4 Drawing Sheets

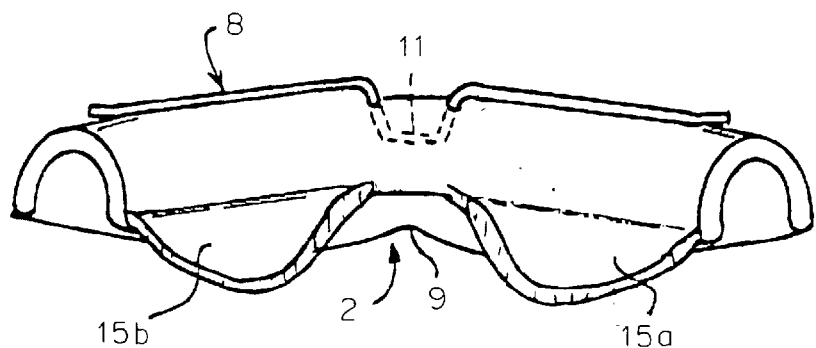
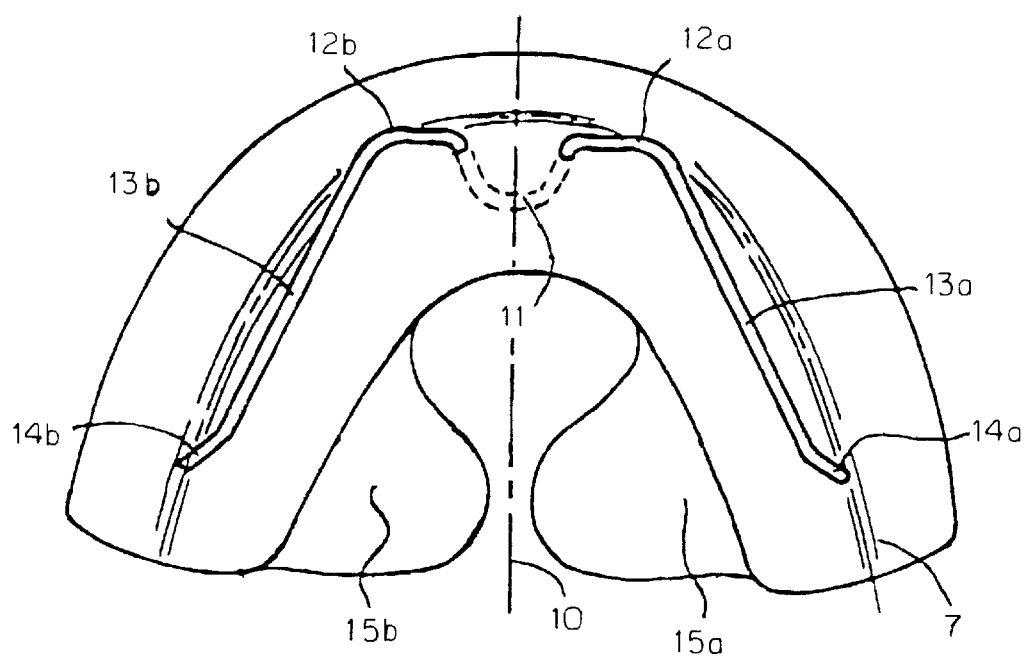

INTRAORAL DEVICE

TECHNICAL FIELD

The invention relates to the field of oral ortheses intended, in particular, to treat snoring and the increase in the resistances of the upper airways during sleep.

PRIOR ART

As is known, snoring is the consequence of a muscular hypotonia which occurs during sleeping. This is because, when the muscles of the jaw are relaxed, the mandible has a natural tendency to move backwards, carrying the tongue towards the rear of the oral cavity as it moves. The oral respiratory tract thus decreases in size and causes turbulence in the respiratory flow, which is responsible for the vibrations of the soft palate and the adjacent soft tissue. This vibration causes the well-known audible phenomenon of snoring.

In some cases, in particular when the dimensions of the tongue are large, this obstruction may be complete, leading therefore to interruptions in the respiration, or apnoeas. These phenomena impair the quality of sleep and the neurovegetative reflexes responsible for arterial, systemic and pulmonary hypertension. Repetition of these apnoeas results for the patient in fatigue on waking and diurnal somnolence. It can thus be seen that this is a true pathology.

In some cases, recourse is made to placing patients, when they sleep, under spontaneous ventilation with continuous positive pressure using a nasal mask. Although effective, this solution nevertheless has the main drawback of needing specific equipment which constitutes a significant restraint.

Another solution which has been proposed for combating these phenomena of apnoeas during sleep consists in performing a resection operation of the soft palate. Besides the fact that this solution constitutes a painful operation, it is not always effective. It also leads to changes in the intrabuccal morphology, which may interfere with swallowing.

Complex instruments, allowing the lower jaw to be advanced by propelling the mandible, have also been proposed for combatting the snoring. However, these systems are integral and operate by fully immobilizing the mandible in an advanced position.

From U.S. Pat. No. 5,365,945, incorporated herein by reference, is known to disclose an intrabuccal device that comprises two shells made of thermoformed plastic material. The first of these shells covers the superior arch of the oral cavity. The second of these shells covers the inferior arch. This device comprises means that act at the said shells and that generate on the mandible a propulsive force oriented in the direction of the mandibular propulsion and in the posteroanterior sense. Moreover, these means allow the shell covering the inferior arch of the mandible to move with a limited degree regard to the shell covering the superior arch of the maxilla.

It has been observed that the mandible moves in the posteroanterior sense at each swallowing and this occurs about two hundred times per night. This movement is impossible with the proposed immobilization systems and with the proposed device, which causes a discomfort in such fitted patients and may cause algo-dysfunctional syndromes of the temporomandibular articulation.

BRIEF DESCRIPTION OF THE INVENTION

The object of the invention is to provide an instrument which permits to keep the mandible in propulsive position, while allowing it to move in relation to the upper maxilla.

The invention relates to an intrabuccal device comprising two shells made of thermoformed plastic material, the first of which respectively covers the superior arch and the second of which covers the inferior arch of a patient's oral cavity, and provided with means that act at the said shells and can generate a mandibular propulsive force oriented in the direction of the mandibular propulsion and in the posteroanterior sense.

The device is characterized in that it allows mandibular retro-propulsion.

In other words, the invention consists in providing the said shells with mechanical means which, in the absence of any other constraint, in particular a physiological one, induce the mandible to move in the forward direction relative to the maxilla.

According to a first embodiment of the invention, these means comprise:

on one of the two shells, above the premolars, a ring that projects beyond the occlusal plane, and on the other shell, a pair of free arms that project beyond the occlusal plane and are parallel to it, these two arms being fastened on the anterior lingual face of the shell and being oriented in the general direction of the occlusion line, these arms being intended to engage and slide in the said rings so as to keep a shift of the mandible to the front of the maxilla, while allowing lateral movements.

In other words, the mandible is held in a propelling position relative to the upper jaw by the interaction of the rings and the arms that are respectively secured to the upper and lower jaw. Moreover, the degree of freedom corresponding to the possibility of the arms sliding inside the rings allows the two maxillae a certain capacity to move.

By interacting with the rings, the arms make it possible to keep a forward shift of the mandible relative to the maxilla while allowing lateral movements, swallowing and breathing through the mouth. In addition, this allows mandibular retrusion in occlusion for convenience, in particular during swallowing. Finally, this system reduces the risks of disorders of the temporomandibular articulation.

To solve the problem of engagement and, above all, that of untimely decoupling, the free ends of the arms are curved towards the vestibular space.

In other words, the two shells constitute independent units which are put together by passing the arms through the rings. Because the ends of the arms are curved, the arms need to be deformed slightly to make them enter the rings, which prevents any untimely decoupling within the patient's mouth.

In view of the great complexity of the kinematics of the temporomandibular articulation, it has been observed that a greater freedom of movement is obtained when each of the rings has an elliptical shape and is placed substantially between the first and second premolars.

In the same way, the capacity for movement is increased when each ring is orthogonal to the occlusion line, and therefore to the direction of the arms.

As already seen, keeping the propulsion is obtained thanks to the spring effect of the free arm/s. This is why in order to increase the elasticity effect further, while improving the strength of the assembly, the arms form the branches of a single V-shaped piece that are directed towards the rear of the mouth and the free ends of which are placed substantially above the first molar.

As is conventional in the field of orthodontics, the rings and the free arms are made of stainless steel.

According to another embodiment of the invention, the two shells receive hooks, intended in turn to receive elastic elements tending to propel the mandible forward. More precisely, the hooks of the lower shell are fastened adjacent to its ends, and advantageously, with the second premolar, whereas the hooks of the upper shell are fastened advantageously above each of the junction regions between the central and lateral incisors.

According to another embodiment of the invention, the generated propulsive force is of magnetic source, permanent magnets being incorporated at the shells in order to generate repulsive forces.

To solve the problem of individualized fitting of this instrument each shell has a top side made of a semirigid thermoformable material, and a bottom side made of a more flexible thermoformable material. In this way, each patient can fit the shell to his own imprint simply by heating, in particular in boiling water, then fitting it over each of his arches.

As can be seen, the invention consists in causing the mandible to propel in order to prevent the tongue from sliding backwards. The advantages of the invention are improved further when, at its two posterior ends, the upper shell has two lobes extending backwards and intended to serve as a support for the lateral portion of the soft palate. In this way, the upper shell has a tendency to move and push the soft palate away in order to prevent it from coming into contact with the tongue.

In complementary fashion, the efficiency of the device is improved if the lower shell has brackets placed in proximity to the free ends of the shell and oriented inwards in the direction of one another, these brackets being intended to bear on the lateral parts of the tongue in order to prevent it from rising. In other words, this avoids the rising of the tongue which is inherent in muscular hypotonia. Of course, these arrangements are particularly advantageous in the case of a patient suffering from macroglossia.

BRIEF DESCRIPTION OF THE DRAWINGS

The way in which the invention is embodied, and the advantages which result therefrom, will emerge more clearly from the description of the illustrative embodiments which follow and are given solely by way of indication and without limitation, supported by the appended figures.

FIGS. 3 and 4 are rear and plan views, respectively, of the lower shell.

FIG. 7 is an exploded outline perspective view of another embodiment of the invention, of which

EMBODIMENTS OF THE INVENTION

Figure 1:
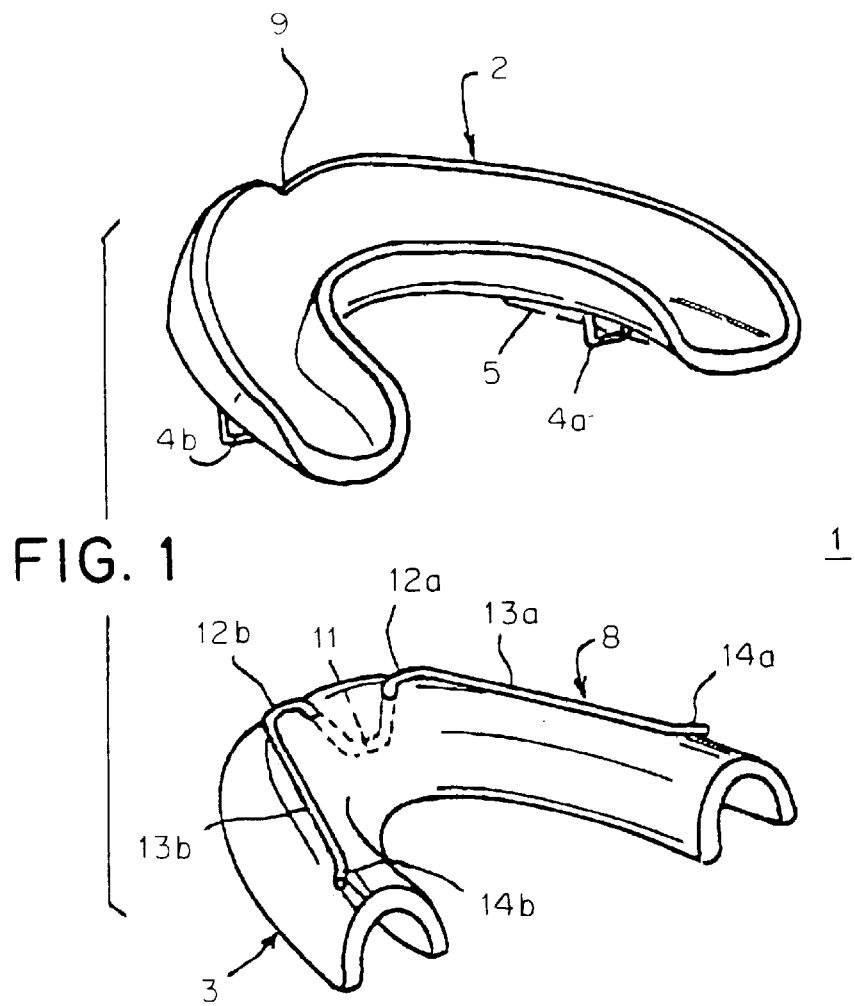
FIG. 1 is an outline perspective view representing the two constituent shells of a first embodiment of the invention, in the decoupled position.

As already stated, the object of the invention is to keep the mandible propelling forwards somewhat while the patient is sleeping. This forward shift makes it possible to move the posterior part of the tongue away from the soft palate, and thus to avoid the risks of snoring which may degenerate into sleep apnoea.

Another combined object of the invention is to leave the mandible with some freedom of movement, in order to make it possible to swallow in the night and breathe through the mouth, without causing a problem for the temporomandibular articulation.

To this end, according to a first embodiment of the invention, the device 1 comprises two shells 2, 3 which are articulated to and disconnectable from one another and have a certain capacity for movement and elasticity between them.

Firstly, the upper shell 2 takes the shape of a channel intended to accommodate the upper arch as far as the second premolar. On each side and at the space between the first and second premolars, this upper shell has a ring 4a, 4b that is directed downwards into the interocclusal space. The ring 4a, 4b has a slightly elliptical shape with a horizontal major axis 5. The plane 6 of the ring is oriented substantially perpendicular to the occlusion line 7, which corresponds to the tooth implantation direction.

Symmetrically, the lower shell 3 forms a channel intended to cover the lower arch, again substantially as far as the second premolars. This lower shell 3 has a protruding metal piece 8 assuming the form of a broken line that is symmetrical with respect to the sagittal plane 10 of the device. This metal piece has a base feet 11 which is secured to the lower shell 3 at the rear of the incisors. This base feet 11 emerges from the shell 3 and extends laterally in a short straight portion 12a, 12b which itself extends in an arm 13a, 13b which is also straight but is longer and ends level with the first molar. This elongate arm ends in a short portion 14a, 14b curved towards the vestibular space. The arrangement of the arm substantially follows the occlusion line 7.

Figure 2:
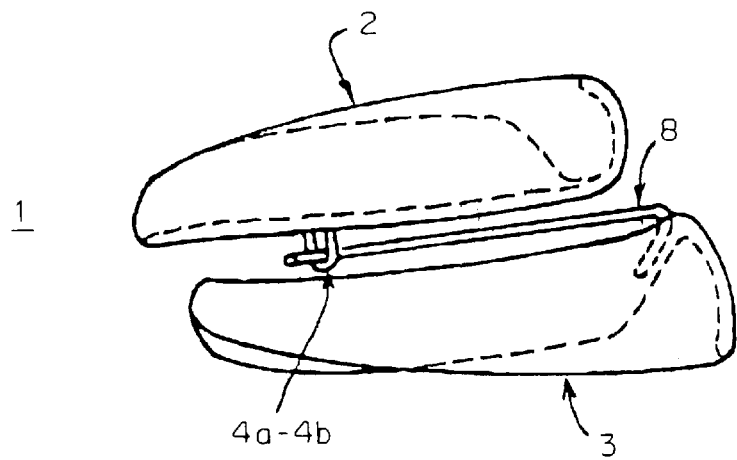
FIG. 2 is a side view showing the device in the coupled position.

When the arms 13a, 13b are introduced into the rings 4a, 4b (see FIG. 2), the two shells 2, 3 form an articulated unit which has a certain capacity for movement forwards as well as to the sides due to lost motion resulting from the arms 13a and 13b being received loosely in the ring 4a and 4b, and When the two shells 2, 3 are placed in such a way that their sagittal planes 9, 10 coincide, the rings 4a, 4b serve as articulation points. The relative motion of the two shells 2, 3 then substantially corresponds to the natural tilting movement existing between the upper maxilla and the mandible.

The dimensions of the rings 4a, 4b, as well as the size of the arms 13a, 13b in relation to the lower shell 3, are calculated in such a way that the position of the mandible is about five millimeters each, in propulsion and in occlusion. These elements function as an actuator for generating a mandibulary neopulsive force.

The reference 9 denotes a rounded recess intended to form a positional reference at the frenula of the upper and lower lips.

As already mentioned, the object of the invention is to increase the oropharyngeal space. To this end, the shells may be equipped with two additional devices.

In a first alternative, which is particularly advantageous in subjects suffering from hypertrophy of the tongue, the lower shell 3 has brackets 15a, 15b fitted on the lingual region and in the direction of the tongue, at the first molar (see FIGS. 3 and 4). These brackets 15a, 15b, positioned substantially at the neck level, bear on the tongue so as to depress it and prevent it from coming into contact with the soft palate. Of course, giving these brackets any particularly anatomical shapes, or having these two brackets form only a single piece that joins the two lingual regions of the lower shell, would not depart from the scope of the invention. In an alternative, these brackets 15a, 15b may be dimensionally adjustable in order to be fitted.

Figure 5:
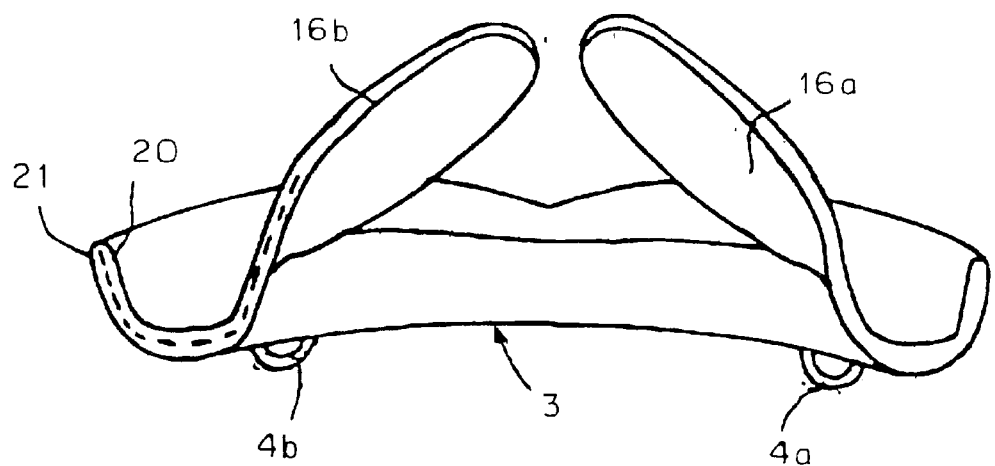
FIGS. 5 and 6 are rear and plan views, respectively, of the upper shell.
Figure 6:
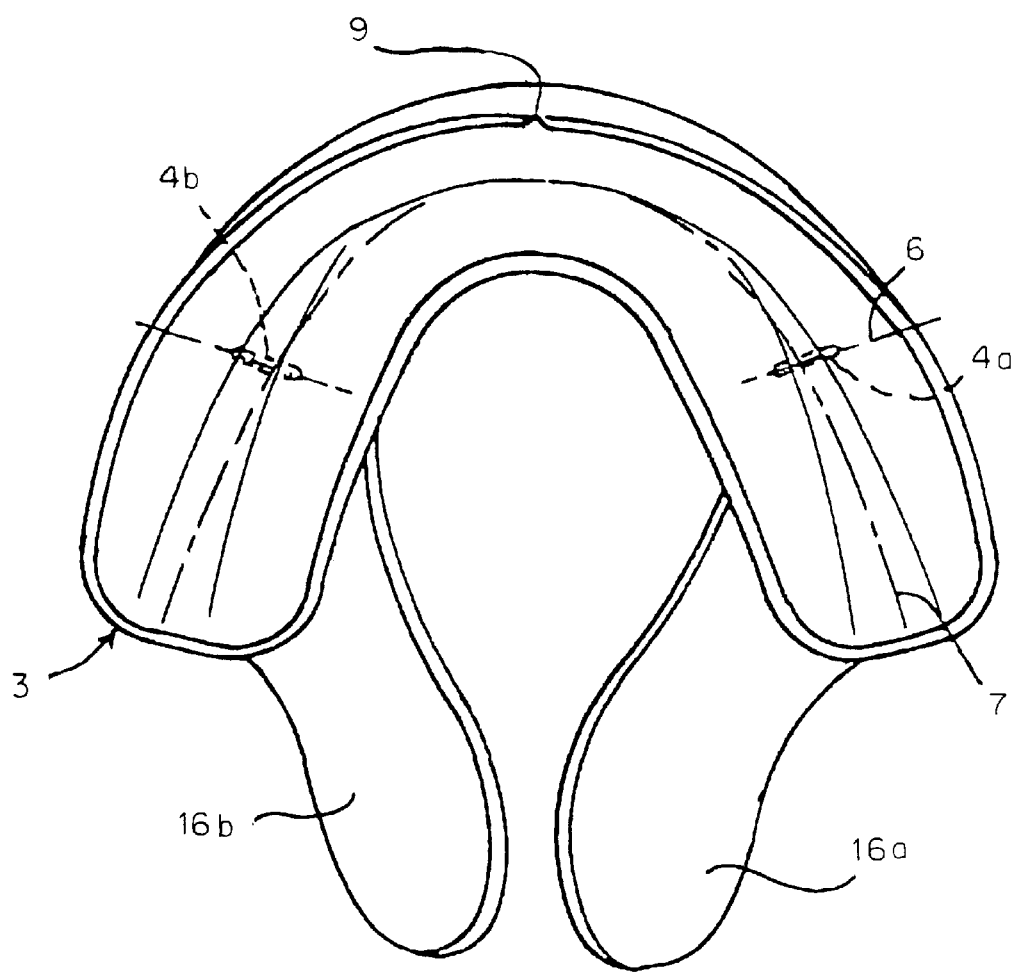

In another alternative, illustrated in FIGS. 5 and 6, the upper shell has two extensions, for example in the form of lobes or in the form of ear 16a, 16b, starting at the posterior lingual end of the said shell. These two extensions 16a, 16b extend backwards and are oriented slightly upwards. Their main function is to bear on the soft palate in order to support it in its lateral regions, still with the aim of increasing the diameter of the oropharyngeal orifice.

Irrespective of the alternative employed, this embodiment that comprises the two metal arms in a V-shape, interacting with the rings provides an actuator that, achieves the generation of a constant force, meeting the intended aim, namely to propel the mandible forwards.

Figure 7:
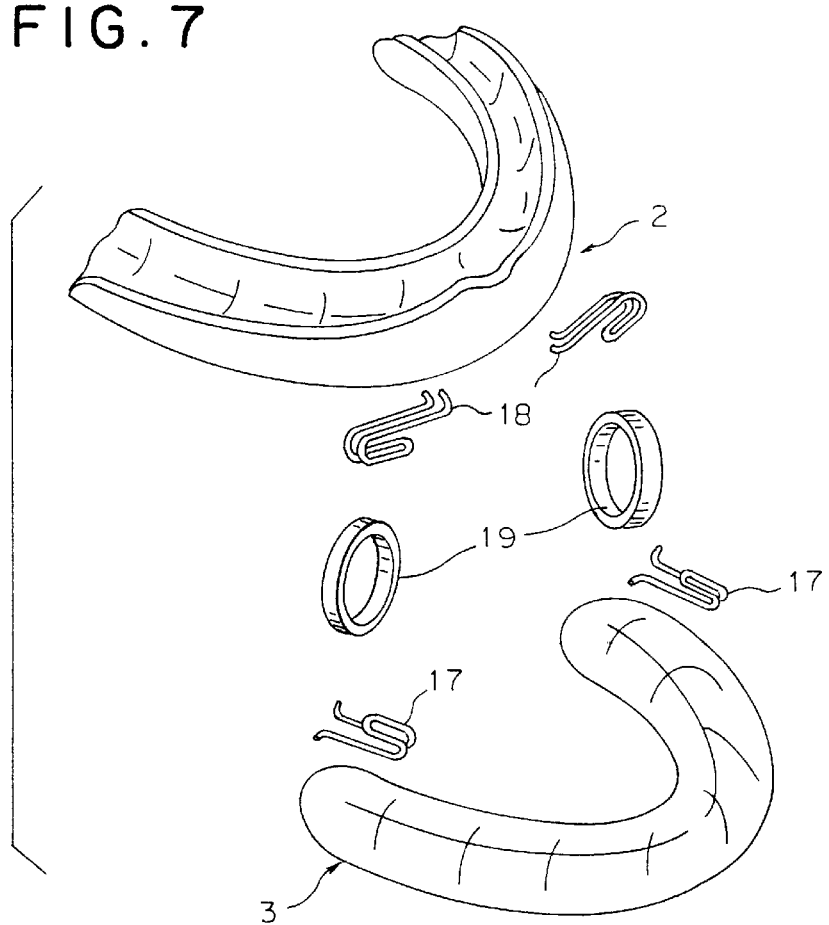
Figure 8:
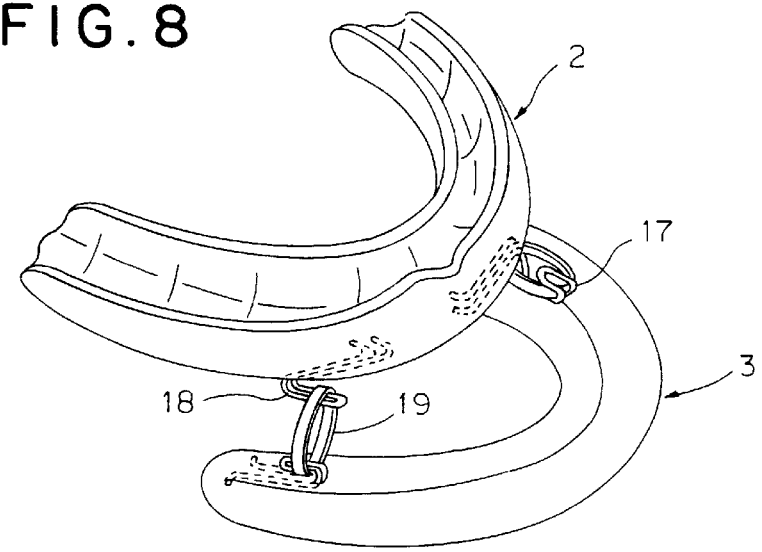
FIG. 8 is a view in the coupled position.

In another embodiment of the invention, represented in conjunction with FIGS. 7 and 8, the metal arms and the rings are replaced by elastic loops and hooks.

Thus, adjacent to its two ends, and more precisely at each of the second premolars, he lower shell 3 is provided with a hook 17 that is directed backwards to provide first elastic band anchoring locations.

Moreover, adjacent to its central portion, and more precisely above each of the junction regions between the central and lateral incisors, the upper shell 2 is provided with a hook 18 that is substantially directed forwards to provide second elastic band anchoring locations.

The hooks 17 of the lower shell 3 are connected to the hooks 18 of the upper shell 2 by elastic loops 19, of a type which is per se well-known in orthodontics and are anchored to the hooks to provide an actuator for generating a mandibular neopulsive force. Their force can be adapted as a function of their cross-section and their diameter. In view of the positioning of the hooks, the loops 19 generate a force, the application point of which is the upper jaw, which induces the mandible to propel forwards, by means of the lower shell.

According to another alternative (not shown), the unit consisting of the elastic loops and the hooks is replaced by permanent magnets to provide an actuator for generating a mandibular neopulsive force. More precisely, each of the shells, respectively the upper shell 2 and the lower shell 3, receives magnetic pellets or cylinders instead of the hooks, with the poles of the magnetic elements fitted at the lower shell and the upper shell which face one another being of opposite types, that is to say north pole-south pole or south pole-north pole, so as to generate an attractive magnetic force that can induce the propulsion of the mandible forwards.

One of the underlying objects of the invention is to permit easy individualized fitting of this device to any type of oral morphology. The two shells are made of biocompatible plastic material, for example polyvinyl chloride, or any type of material which has the same capacities for anatomical contact. In order to make individualized positioning and fitting of this device easier, each shell is formed by two parts that have different hardnesses. The top side 21, or exterior region of the channel is made of a material having a Shore D hardness of about 80, whereas the interior part 20 of the channel, which comes into contact with the arch (or the bottom side), is made of a material having a Shore D hardness of the order of 40. Shaping each of the shells thus constitutes a straightforward operation which does not require any specialized equipment, such as known devices for taking imprints. Indeed, simple immersion in boiling water is enough to soften the bottom side 20, while keeping the top side 21 sufficiently rigid. Thus, applying the softened inner surface 20 to the arch by simple pressure gives it a shape corresponding to the shape of the patient's arch.

Good results are obtained when the top side part 21 has a thickness of one millimeter, whereas the bottom side 20 has a thickness of two millimeters. This avoids an interstitial filling phenomenon which constitutes a particular discomfort for patients who wear dental prostheses.

As regards the rings 4a, 4b and the arms 13a, 13b, use is made of steel wires, respectively eight tenths and fourteen tenths of a millimeter, of 18/8 steel which is commonly used in orthodontics.

In another individualized embodiment, the device of the invention may be produced with conventional means. As is known, an imprint of the maxilla and the mandible is first of all taken, taking care to hold back the soft palate when taking the imprint of the maxilla. A suitable system is then used to record the occlusion with the mandible in a propelled position, without the occurrence of temporomandibular articulation pain, generally five millimeters with an interocclusal clearance of five millimeters. The mouldings thus obtained are mounted in extra-hard plaster under vacuum, then mounted on the articulator in the position defined by the aforementioned recording.

The maxilla and mandibular pieces are then shaped, in particular by thermoforming, following the outline at half coronal height of all the teeth on the vestibular side, or at full height of the teeth on the lingual side. Two lobes support the soft palate as widely as possible without leading to nausea reflexes.

The above description shows that the device according to the invention has a number of advantages. Mention may, in particular, be made of the combination of mandibular propulsion combined with the possibility of lateral movements. Furthermore, the installation of all the elements which provide the articulation is particularly well-suited to the morphology of the temporomandibular articulation. Lastly, the simplicity of the device allows it to be fitted individually without any specialized intervention.

Although the invention has been described with reference to its application for the treatment of snorers, with or without sleep apnoea, the device may also be of very particular benefit in orthopaedic and orthodontic treatment. In particular, mention may be made of the possibility of using it as a hyperpropulsor for subjects afflicted with mandibular retrusion. Furthermore, the invention also encompasses the alternative in which the arms are fitted on the upper shell whilst the rings are fitted on the lower shell, so that the upper shell is naturally pushed forward, in particular for the treatment of prognathic individuals.

What is claimed is:

1. An intrabuccal device for insertion into a patient's oral cavity to control the position of the patient's mandible with respect to the patient's maxilla, which oral cavity has a superior arch, an inferior arch premolars and an occlusal plane, the device comprising:

two shells made of thermoformed plastic material, the first of which covers the superior arch, and the second of which covers the interior arch, the device including an actuator acting on the shells for generating a mandibular propulsive force oriented in the direction of mandibular propulsion in a posterior-anterior sense and allowing a mandibular retrusion force, wherein the actuator comprises:

on one of the two shells, adjacent to the premolars in the oral cavity, a pair of rings that project beyond the occlusal plane, and on the other shell, a pair of free arms that project beyond the occlusal plane and are parallel thereto, the two arms being fastened on an anterior lingual face of the shell and being oriented in the general direction of the occlusion line, the arms engaging and sliding in the rings to keep a shift of the mandible to the front of the maxilla while allowing lateral movements.

2. An intrabuccal device according to claim 1, wherein the free ends of the arms are curved towards the vestibular space.

3. An intrabuccal device according to claim 2, wherein each of the rings has an elliptical shape and is placed between the first and second premolars.

4. An intrabuccal device according to claim 3, wherein each of the rings is orthogonal to the occlusion line.

5. An intrabuccal device according to claim 4, wherein the arms form the branches of a single V-shaped piece directed towards the rear of the mouth, the free ends of which are placed above the first molar.

6. An intrabuccal device according to claim 5, wherein the rings and the free arms are made of stainless steel.

7. An intrabuccal device according to claim 1, wherein each of the rings has an elliptical shape and is placed between the first and second premolars.

8. An intrabuccal device according to claim 1, wherein each of the rings is orthogonal to the occlusion line.

9. An intrabuccal device according to claim 1, wherein the arms form the branches of a single V-shaped piece directed towards the rear of the mouth, the free ends of which are placed above the first molar.

10. An intrabuccal device according to claim 1, wherein the rings and the free arms are made of stainless steel.

11. An intrabuccal device according to claim 1, wherein each shell has a top side made of a semirigid thermoformable material, and a bottom side made of a more flexible thermoformable material.

12. An intrabuccal device according to claim 1, wherein at its two posterior ends, the upper shell has two extensions which project backwards and are intended to serve as a support for the lateral portions of the soft palate.

13. An intrabuccal device according to claim 1, wherein the lower shell has brackets placed in proximity to the posterior ends of the shell and oriented inwards in the direction of one another, these lobes bearing on the lateral parts of the tongue in order to prevent the tongue from rising.

14. An intrabuccal device for insertion into a patient's oral cavity to control the position of the patient's mandible which cavity has a superior arch and an inferior arch, comprising:

two shells made of thermoformed plastic material the first of which covers the superior arch, and the second of which covers the interior arch, each shell have a top side made of a semi-rigid thermoformable material and a bottom side made of a more flexible material, wherein the device includes an actuator acting on the shells for generating a mandibular propulsive force oriented in the direction of mandibular propulsion in a posterior-anterior sense, the actuator comprising magnetic elements fastened to the shells and oriented in such a way as to generate an attractive magnetic force that can induce propulsion of the mandible forwards.

15. An intrabuccal device according to claim 14, wherein, at its two posterior ends, the upper shell has two extensions which project backwards and are intended to serve as a support for the lateral portions of the soft palate.

16. An intrabuccal device according to claim 15, wherein the lower shell has brackets placed in proximity to the posterior ends of the shell and oriented inwards in the direction of one another, these lobes bearing on the lateral parts of the tongue in order to prevent the tongue from rising.

* * * * *

UNITED STATES PATENT AND TRADEMARK OFFICE
CERTIFICATE OF CORRECTION

PATENT NO. : 6,450,167 B1 Page 1 of 1
DATED : September 17, 2002
INVENTOR(S) : David et al.

It is certified that error appears in the above-identified patent and that said Letters Patent is hereby corrected as shown below:

<u>Column 8,</u>
Line 28, change "15" to -- 1 --.

Signed and Sealed this

Twelfth Day of August, 2003

JAMES E. ROGAN
*Director of the United States Patent and Trademark Office*